(12) United States Patent
Lee et al.

(10) Patent No.: US 6,951,740 B2
(45) Date of Patent: Oct. 4, 2005

(54) METHOD FOR MASS-PRODUCTION OF TARGET PROTEIN BY REGULATING THE EXPRESSION OF CHAPERONE PROTEIN

(75) Inventors: Gyun Min Lee, Taejon (KR); Sun Ok Hwang, Seoul (KR); Joo Young Chung, Yongin-si (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 309 days.

(21) Appl. No.: 10/396,869

(22) Filed: Mar. 25, 2003

(65) Prior Publication Data
US 2004/0073002 A1 Apr. 15, 2004

(30) Foreign Application Priority Data

Sep. 30, 2002 (KR) .................... 10-2002-0059503

(51) Int. Cl.[7] .......................... C12P 21/02; C12N 15/63; C12N 5/10
(52) U.S. Cl. ................... 435/69.1; 435/320.1; 435/325
(58) Field of Search ............................. 435/69.1, 320.1, 435/325

(56) References Cited

U.S. PATENT DOCUMENTS

2005/0081256 A1 * 4/2005 Forsberg et al. .............. 800/14

OTHER PUBLICATIONS

Raymond Davis et al., "Effect of PDI Overexpression on Recombinant Protein Secretion in CHO Cells", Biotechnol. Prog. 2000, 16, 736–743.

Andrew J. Dorner et al., "Overexpression of GRP78 mitigates stress induction of glucose regulated proteins and blocks secretion of selective proteins in Chinese hamster ovary cells", The EMBO Journal, vol. 11, No. 4, pp. 1563–1571, 1992.

* cited by examiner

Primary Examiner—Robert A. Wax
(74) Attorney, Agent, or Firm—Lucas & Mercanti, LLP

(57) ABSTRACT

The present invention relates to a method for mass-production of target protein, particularly to a method for mass-production of trombopoietin by regulating the expression of chaperone protein.

15 Claims, 13 Drawing Sheets

A

B

C

METHOD FOR MASS-PRODUCTION OF TARGET PROTEIN BY REGULATING THE EXPRESSION OF CHAPERONE PROTEIN

This patent application claims a benefit of priority from Korean Patent Application No. 2002-59503 filed Sep. 30, 2002, the contents of which are incorporated herein by reference.

FIELD OF THE INVENTION

The present invention relates to a method for mass-production of target protein, particularly to a method for mass-production of trombopoietin by regulating the expression of chaperone protein.

BACKGROUND OF THE INVENTION

The molecular chaperone that is known as a heat shock protein functions to prevent incorrect structure forming that is resulted from the interaction between subdomains of a polypeptide or between a polypeptide and other molecules. Although molecular chaperone mediates the perfect assembling of a polypeptide, it has nothing to do with the assembled protein because it is no more a subunit of a protein once the assembling procedure is finished.

The molecular chaperone helps a polypeptide assemble itself by obstructing alternative assembly pathways forming a nonfunctional structure and mediates folding of a newly synthesized polypeptide chain. The molecular chaperone is separated from a protein once the protein matrix has not a misfolding conformation any more. These molecular chaperones are characterized by the ability to bind a partly folded intermediary metabolite temporarily during the folding and assembling procedure of a protein. Precisely, they do not bind to a completely folded and assembled conformation and function to make an effective folding and assembling procedure by preventing premature folding and gathering intermediary metabolites.

As explained hereinbefore, the molecular chaperone has been confirmed to help a protein have a normal stable confirmation by preventing misfolding of proteins largely. Thus, the molecular chaperone is confirmed to be an important factor to promote the productivity of proteins.

Recently, lots of medical supplies using recombinant proteins are being produced. Particularly, such medical supplies are produced by transfecting gene of interest into host cells. For the stable market of medical supplies, it is important to mass-produce a recombinant protein, so called a target protein, which triggers vigorous studies on the way to promote the productivity of foreign proteins from many host cell lines. As an example, studies are undergoing to promote the productivity of foreign proteins using CHO cell line. The final concentration of target proteins produced from CHO cell line is affected by the density of live cells producing target proteins and specific production rate as seen in the below <Mathematical Formula 1>.

Final protein concentration=Cell density×Specific production rate     <Mathematical Formula 1>

It has been a major study object to increase cell density by taking advantage of batch culture for culturing cells producing target proteins since specific production rate has been regarded to be a native factor to a cell and not to be changed. However, in order to increase specific production rate, methods to increase production speed of cells using high osmotic pressure media or gene amplification system like dihydrofolate reductase(dhfr)/methotrexate(MTX) and glutamine synthatase(GS)/methionine sulfoximine(MSX) have been tried. But those methods are to increase the concentration of final product by just making the best of either cell density determining the concentration of target protein or specific production rate. Besides, when gene amplification system is used, the copy number of recombinant gene increases only to a limited level and thus, the productivity of recombinant protein does not increase further over the level, resulting in just saturation. When high osmotic pressure medium is used, specific production rate goes up, though, cell growth and survival rate decreases. The reason why the protein productivity is in saturation even though the copy number of gene increases continuously seems to be because of speed determining step of endoplasmic reticulum (Fred J. Stevens and Yair Argon, *Cell & Developmental Biology*, 1999, 10, 443–454). So an attempt to introduce molecular chaperone, a factor determining protein secretion speed in endoplasmic reticulum, to cells producing target proteins has been made in order to increase over-expression of chaperone therein. But over-expression of chaperone rather brought negative effects. For example, over-expression of PDI protein in CHO cells held TNFR:Fc in endoplasmic reticulum, resulting in the decrease of secretion thereof (Raymond Davis, et al., *Biotechnology Progress*, 2000, 16, 736–743), and over-expression of GRP78 in CHO cells inhibited the secretion of mutant forms of von Willebrand factor and factor VIII (Dorner, A. J. et al., *EMBO J.*, 1992, 11, 1563–1571).

Thus, another attempt to use a gene expression regulating system has been made again. Among many gene expression-regulating systems, Tet-Off system has been widely used because the system has fewer side effects and can regulate gene expression selectively. Tet-Off system is based on a regulating element of tetracycline resistant operon of *Escherichia coli*. This operon comprises transactivator (tTA) regulated by tetracycline and a promoter depending on tTA. The promoter does not work at all when tetracycline (ex: doxycycline or mynocycline) is there and is only activated in the absence of tetracycline (FIG. 1). Tet-Off system draws an attention since gene expression in mammalian cells can be regulated, the most exact on/off regulation is possible and the regulation with inexpensive tetracycline or doxycycline is also possible with the system, etc.

Thus, the present inventors completed this invention by confirming the fact that the production of target protein is regulated or the mass-production thereof is possible by regulating the expression of chaperone in cells producing target protein by introducing Tet-Off system that regulates the expression of chaperone known to help the protein secretion in endoplasmic reticulum.

SUMMARY OF THE INVENTION

The present invention provides an expression vector containing a gene encoding chaperone protein and tetracycline respond element. It is preferable for a gene encoding chaperone protein to be ERp57 gene represented by SEQ. ID. No 7 or CNX/CRT gene represented by SEQ. ID. No 8/9.

The present invention also provides a transformant in which the above expression vector is transfected in a cell line producing trombopoietin. The cell line producing trombopoietin is preferably to be a CHO cell line producing trombopoietin.

The present invention further provides a method for the mass-production of trombopoietin, which comprises the following steps:

1) Constructing an expression vector containing a gene encoding chaperone protein and tetracycline respond element;

2) Preparing a transformant by transfecting a cell line producing trombopoietin with the expression vector of the above step 1;

3) Mass-producing of trombopoietin by culturing the transformant of the above step 2 with different concentrations of tetracycline.

BRIEF DESCRIPTION OF THE DRAWINGS

The application of the preferred embodiments of the present invention is best understood with reference to the accompanying drawings, wherein.

■: Doxycycline treated,

☐: Doxycycline not treated

Figure 3:
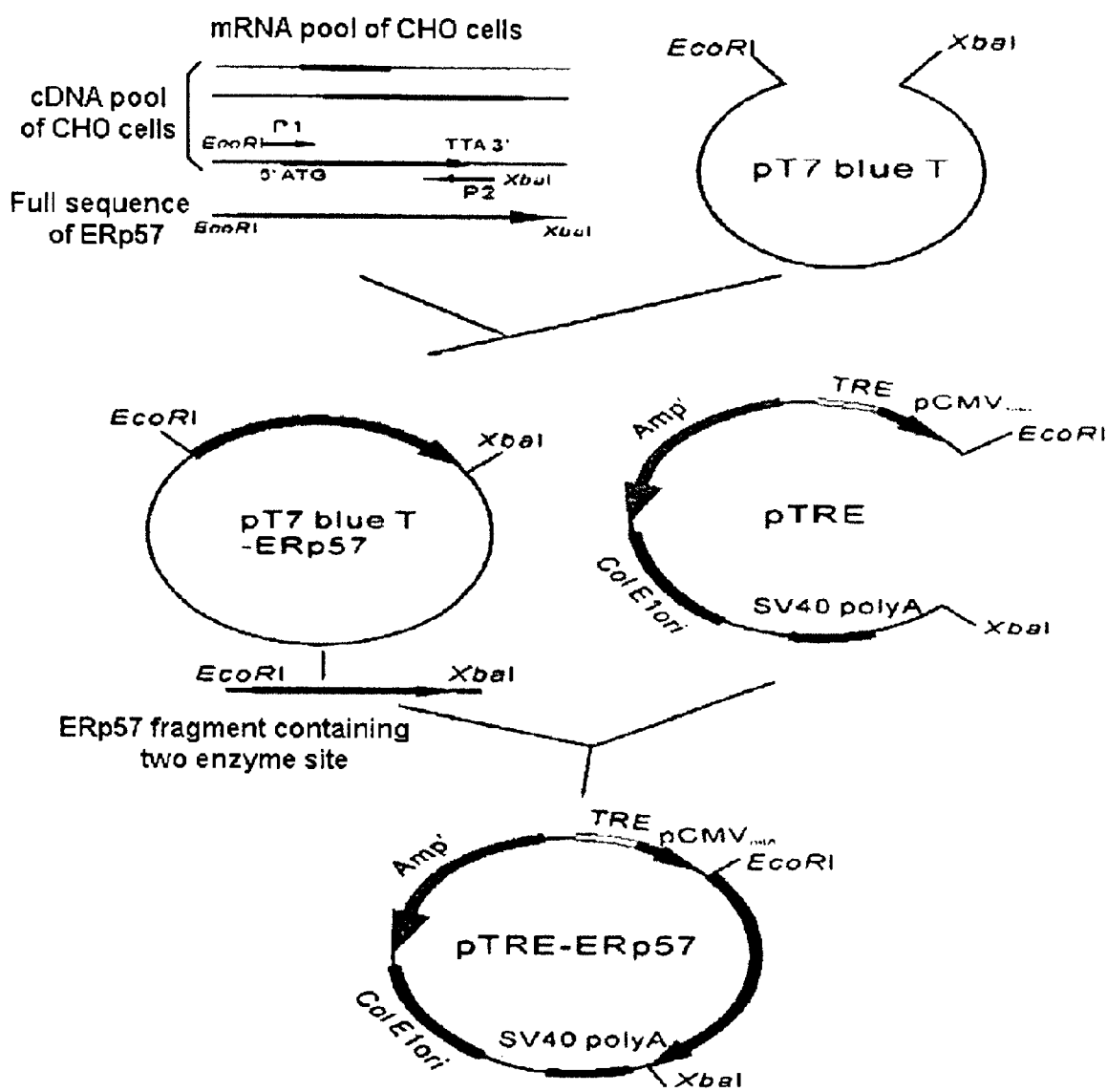
Figure 4:
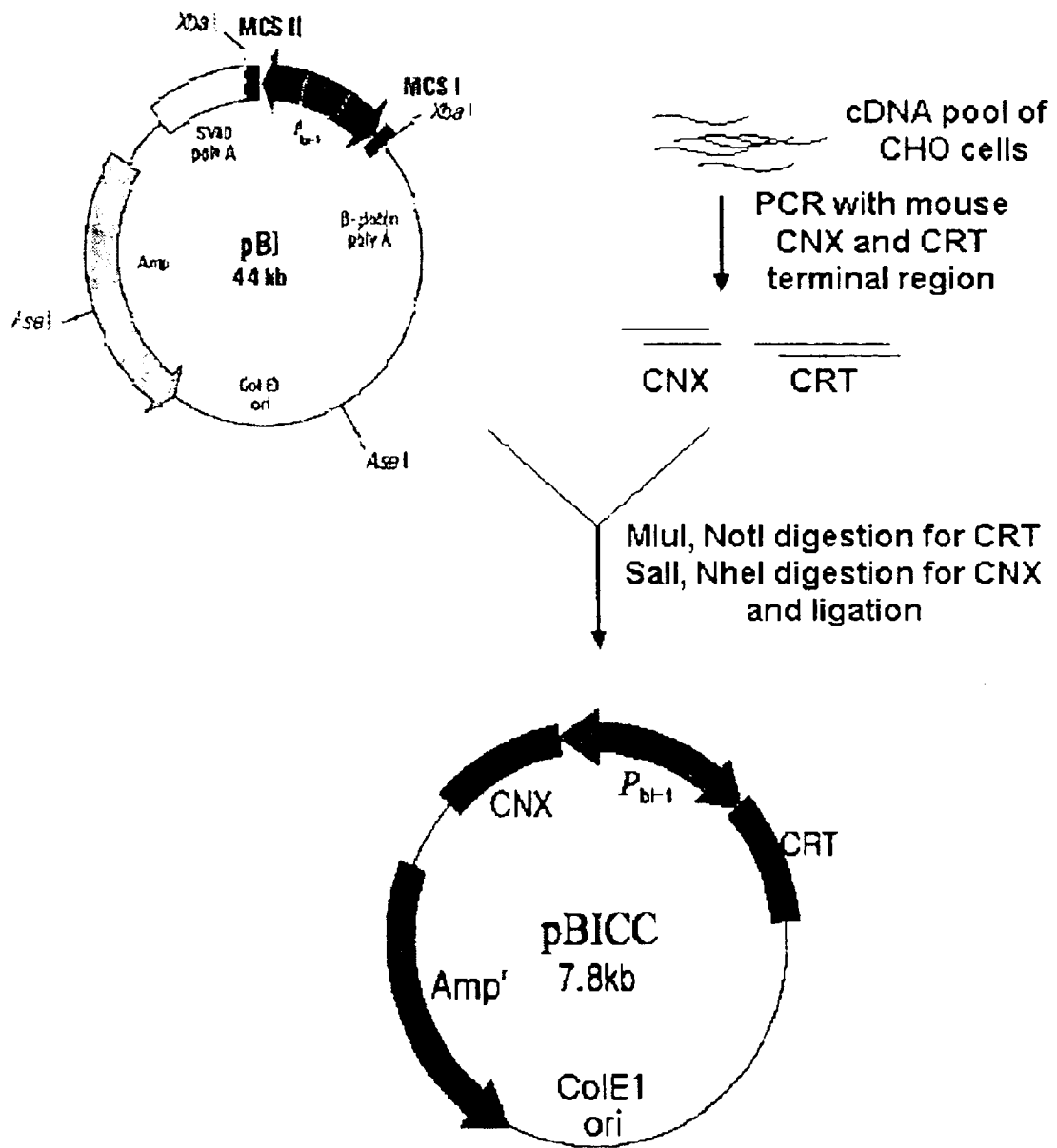

FIG. 3 is a schematic representation of procedure for the establishment of pTRE-Erp57 expression vector for the regulation of Erp57 protein by concentration of doxycycline;

FIG. 4 is a schematic representation of procedure for the establishment of pBICC expression vector for the co-expression of CRT/CNX;

FIGS. 5A–C is a set of photographs and a graph showing the selecting procedure of clones with doxycycline-regulated Erp57 expression;

5A: Western blot analysis of ERp57 in nine representative clones,

5B: TPO concentrations in culture supernatants,

5C: Western blot analysis of Erp57 in selected clones (16, 19 and 23) and a negative control cell (TPO-33-Tet-Off®)

Figure 6:
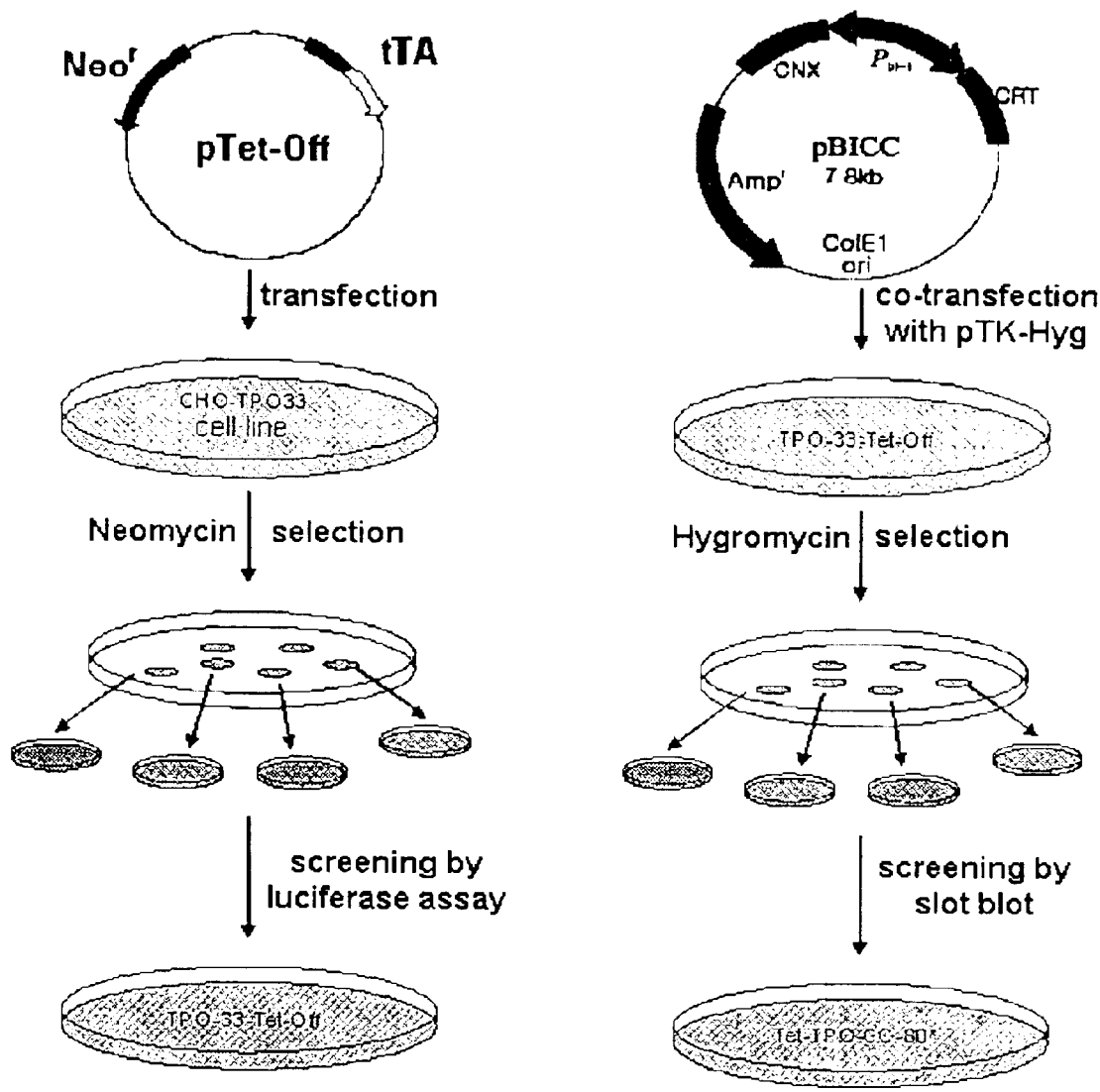
Figure 8:
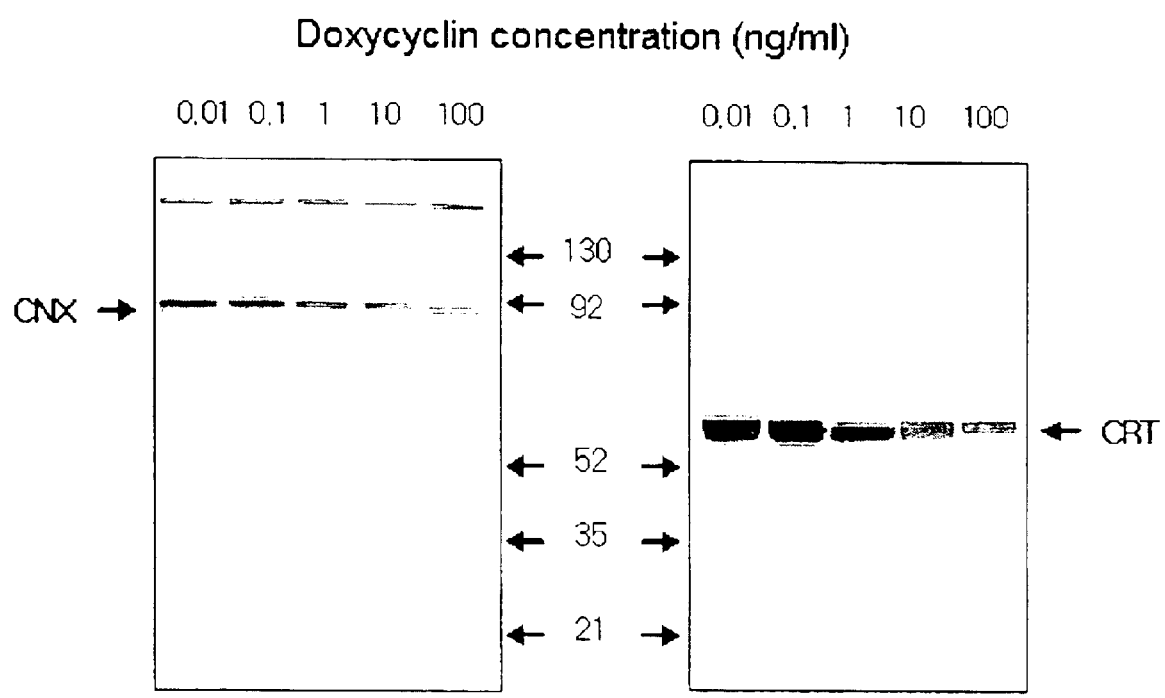
Figure 9:
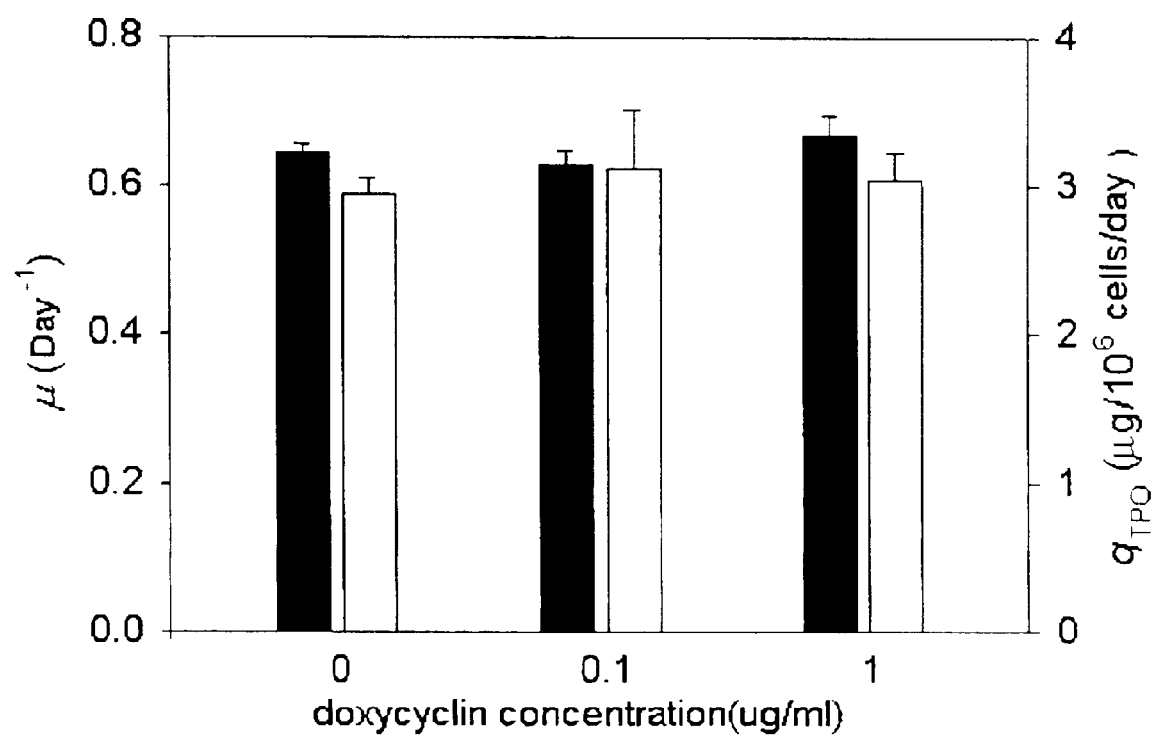
Figure 10:
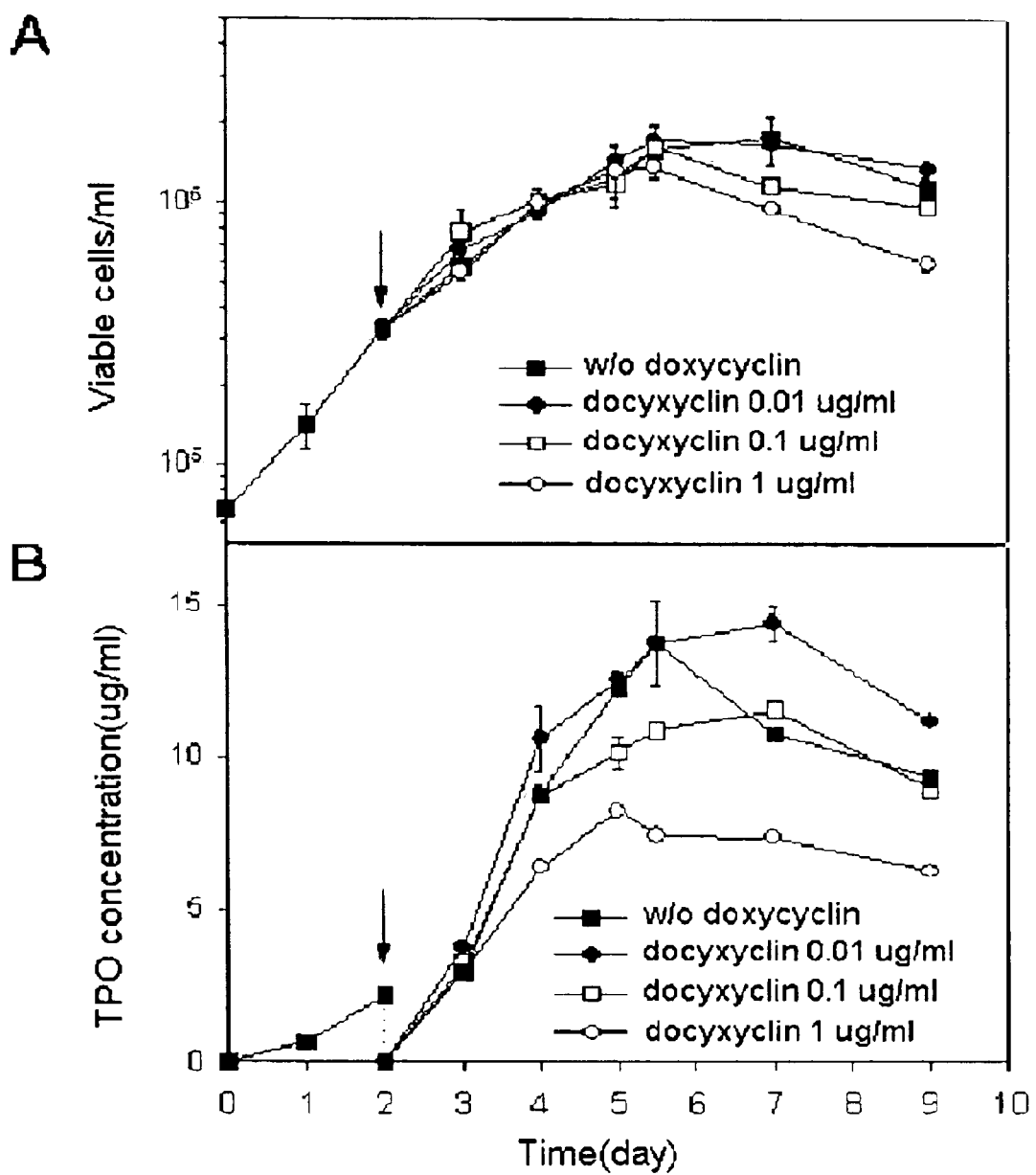
Figure 11:
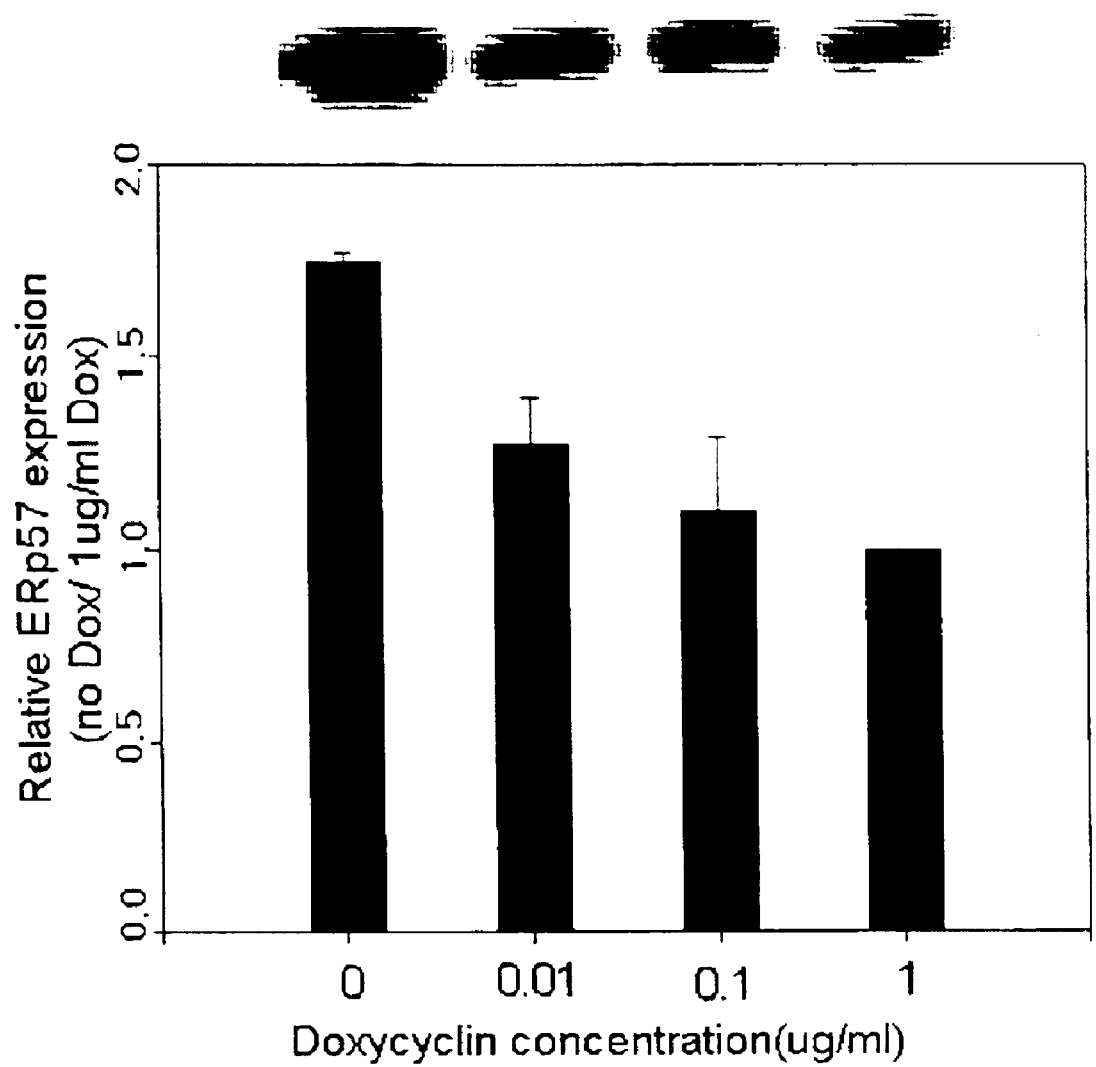

FIG. 6 is a diagram showing the preparation procedure of Tet-TPO-CC-80*, a CHO cell line producing doxycycline-regulated TPO, by inserting CRT/CNX expressing pBICC vector into TPO-33-Tet-Off® cells;

FIGS. 7A–B shows a photograph (A) of slotblot performed to select Tet-TPO-CC-80* clone in which CNX expression was largely affected by doxycycline and a graph 7(B) representing the relative quantity of expressed CNX resulted from the slotblot;

FIG. 8 is a set of photographs of Western blot showing that the expression of CRT and CNX is exquisitely regulated by doxycycline in Tet-TPO-CC-80* cell clone;

FIG. 9 is a graph showing the comparison of the cell growth and the TPO productivity of control group cells (TPO-33-Tet-Off®) cultured in the presence of 0, 0.1 and 1 µg/ml doxycycline;

FIG. 10 is a set of graphs showing the numbers of surviving cells (A) and the TPO productivity (B) of Tet-TPO-ERp57-80* cells cultured in the presence of 0, 0.001, 0.1 and 1 µg/ml doxycycline;

FIG. 11 is a photograph of Western blot (upper panel) analyzing the ERp57 expression in Tet-TPO-ERp57-80* cells cultured in the presence of 0, 0.01, 0.1 and 1 µg/ml doxycycline, and a graph (lower panel) representing relative ERp57 expression amount obtained through the Western blot by dividing each expression amount by that in the presence of 1 µg/ml doxycycline;

FIGS. 12A–B is a set of graphs showing the number of surviving cells (12A) and the TPO productivity (12B) of Tet-TPO-CC-80* cells batch-cultured in the presence of 0, 0.001 and 2 µg/ml doxycycline;

● treated with 2 µg/ml doxycycline,

0: treated with 0.001 µg/ml doxycycline,

▼: treated with 0 µg/ml doxycycline

Figure 13:
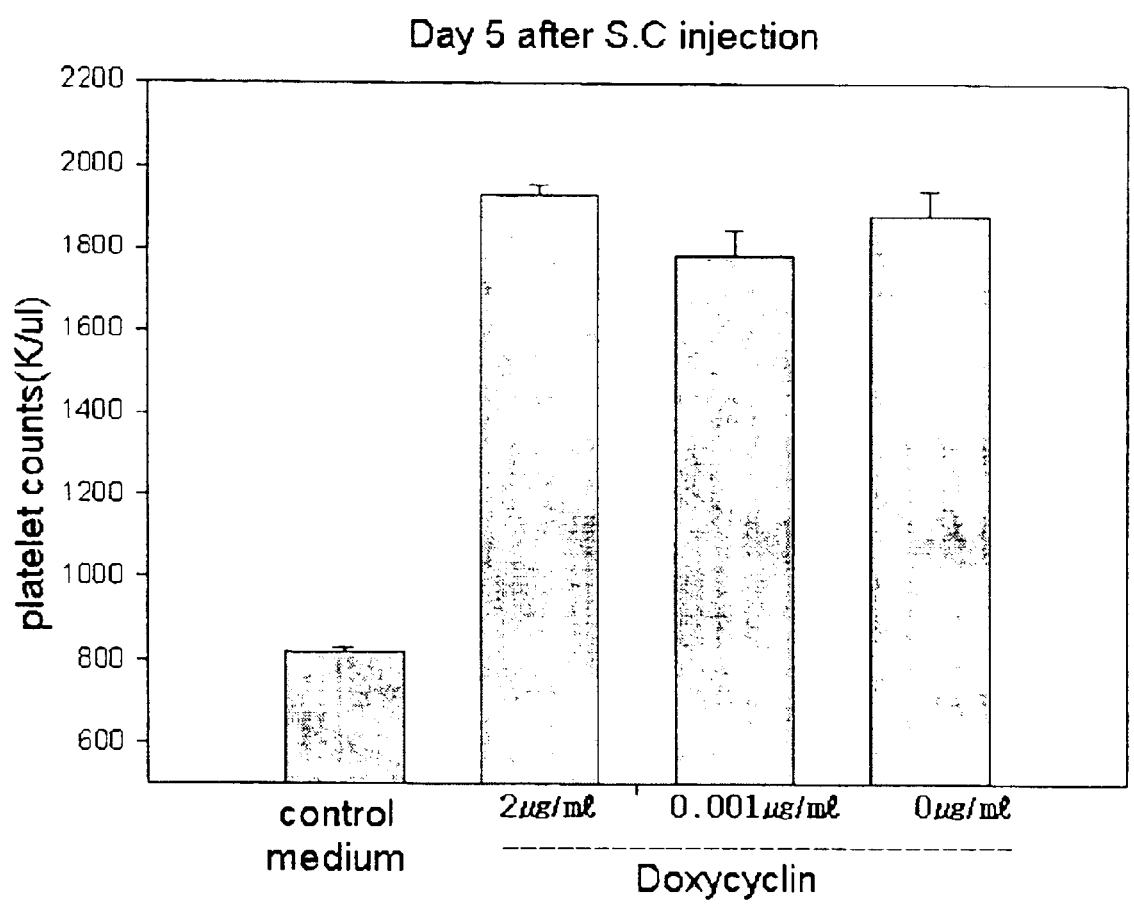

FIG. 13 is a graph showing the platelet counts obtained 5 days after injecting hypodermically Tet-TPO-CC-80* cell culture solution cultured in the presence of 0, 0.001 and 2 µg/ml doxycycline.

DETAILED DESCRIPTION OF PREFERRED EMBODIMENTS

The present invention provides an expression vector containing a gene encoding chaperone protein and tetracycline respond element.

The expression vector of the present invention is characterized by including a gene encoding chaperone protein and tetracycline respond element. The gene encoding chaperone protein is originated from CHO(Chinese hamster ovary, reffered "CHO" hereinafter) cell line and is preferably ERp57 or CRT/CNX gene, but not always limited thereto. Other chaperone genes can be used as well. In the preferred embodiment of the present invention, a gene encoding ERp57 or CRT/CNX protein was separated from CHO cell line and used. In order to construct an expression vector for ERp57 protein, a kind of chaperone protein, the present inventors constructed a recombinant vector by inserting ERp57 cDNA represented by SEQ. ID. No 7 into pTRE vector containing tetracycline respond element and then named thereof "pTRE-ERp57" (see FIG. 3). The present inventors have deposited the above expression vector, pTRE-ERp57, at Gene Bank of Korea Research Institute of Bioscience and Biotechnology on Sep. 27, 2002 (Accession No: KCTC 10345BP). Next, the present inventors constructed another recombinant vector by inserting CNX cDNA represented by SEQ. ID. No 8 into pBI Tet vector containing tetracycline respond element in order to prepare an expression vector for another chaperone protein CRT/CNX, and then named thereof "pBI-C". Again, in order to induce simultaneous expression of CRT in addition to CNX, the present inventors prepared a recombinant vector by inserting CRT cDNA represented by SEQ. ID. No 9 into the above pBI-C vector, and then named thereof "pBICC" (see FIG. 3).

The present invention also provides a transformant in which the above expression vector is transfected in a cell line producing target protein. In the preferred embodiment of the present invention, trombopoietin was used as a target protein.

The transformed cell line of the present invention was prepared by transfecting CHO cell line producing trombopoietin, so that gene expression thereof is to be regulated by tetracycline. In the preferred embodiment of the present invention, the present inventors introduced Tet-Off® system, a vector that regulates gene expression with the concentration of tetracycline, into a CHO cell line producing trombopoietin. The above Tet-Off® system makes gene expression increase in the absence of tetracycline, but makes it decrease in the presence of tetracycline. The present inventors prepared cell line in which the production and secretion of trombopoietin could be regulated by regulating tetracycline concentration as CHO cell line to which Tet-Off® system was introduced was cultured, and named thereof "TPO-33-Tet-Off®". The present inventors have confirmed that gene expression in the cell line was suppressed as the concentration of tetracycline increased (see FIG. 2).

The present inventors also prepared a transformed cell line by inserting a vector containing tetracycline respond element and a gene encoding chaperone protein ERp57 into CHO cell line producing trombopoietin in which Tet-Off® vector was already introduced. The present inventors obtained cell clone #16 in which the expression of ERp57 protein was regulated sensitively, and named thereof "Tet-TPO-ERp57-80*". The present inventors prepared another transformed cell line by inserting a vector including a gene encoding CRT/CNX into CHO cell line producing trombopoietin in which Tet-Off® vector was already introduced and named thereof "Tet-TPO-CC-80*" (see FIG. 6).

The present invention further provides a method for the mass-production of target protein using the above transformant.

The method for the mass-production of target protein of the present invention comprises the following steps:
1) Constructing an expression vector containing a gene encoding chaperone protein and tetracycline respond element;
2) Preparing a transformant by transfecting a cell line producing target protein with the expression vector of the above step 1; and
3) Culturing the transformant of the above step 2 with different concentrations of tetracycline.

As for the step 1, a chaperone protein is preferably to be ERp57 or CRT/CNX and ought to be originated from a CHO cell line. In the preferred embodiment of the present invention, ERp57 represented by SEQ. ID. No 7, CRT represented by SEQ. ID. No 8 and CNX represented by SEQ. ID. No 9 were used.

As for the step 2, a cell line producing target protein is preferably to be a cell line in which Tet-off vector regulating the expression of a gene encoding target protein with tetracycline concentration is introduced. The target protein can be selected from a group consisting of trombopoietin, erythropoietin and therapeutic antibody, but not always limited thereto. In the preferred embodiment of the present invention, trombopoietin was used as target protein.

As for the step 3, tried different concentrations of tetracycline for the culture. As tetracycline concentration decreased, the expression of chaperone protein included in the vector of the above step 1 increased, resulting in the promotion of the productivity of target protein. At that time, tetracycline could be selected from a group consisting of doxycycline and mynocycline, and doxycycline was preferred. In the preferred embodiment of the present invention, the present inventors treated the transformant prepared in the above step 2 with different concentrations of doxycycline and further cultured, after which measured the amount of trombopoietin produced from the above cells. As a result, the expression of ERp57 or CRT/CNX increased as doxycycline concentration decreased, leading to the promotion of trombopoietin productivity (see FIG. 10 and FIG. 12).

As explained in hereinbefore, the method of the present invention is proved to be very effective for the mass-production of a target protein.

EXAMPLES

Practical and presently preferred embodiments of the present invention are illustrative as shown in the following Examples. It will be appreciated, however, that those skilled in the art, on consideration of this disclosure, may make modifications and improvements within the spirit and scope of the present invention.

Example 1

Preparation of CHO Cell Clone (TPO-33-Tet-Off®) Regulated by Doxycycline

The present inventors prepared Tet-Off® CHO cell line by introducing Tet-Off® system in CHO cells to regulate the expression of thrombopoietin (referred "TPO" hereinafter) with doxycycline. Particularly, added 3 ml of IMDM media (Iscove's modified Dulbecco's media, Gibco, Grand Island, N.Y.) containing 80 nM methotrexate (referred "MTX" hereinafter; Sigma) and 10% dialyzed Fetal Bovine Serum (referred "dFBS" hereinafter, Gibco., Grand Island, N.Y.) into 6 well culture plate (Nunc, Denmark). Inoculated TPO-33 CHO cell line (Daewoong Pharmaceutical Co. Ltd., Korea), a TPO analogue producing cell line, thereto at the density of $10^5$ cell/ml. After 24 hours, transfected the TPO-33 CHO cells with pTet-Off® vector (Clontech, Palo Alto, Calif.), a Tet-Off® system expression vector having regulatory element of the tetracycline-resistance operon of *Escherichia coli* and its gene expression is regulated by tetracycline, using lipofectamine. Selected transfected cells while culturing the cells in IMDM containing 500 µg/ml of G418 (Sigma), 10% dFBS and 80 nM of MTX for 2–3 weeks. To screen the stable Tet-Off CHO cell line, constructed transformants containing luciferase gene by transfecting the cells again with pBI-Luc vector (Clontech) having luciferase. When the above transformant was not treated with tetracycline, the luciferase activity increased and when the transformant was treated with tetracycline, the luciferase activity decreased. Therefore, it was possible to select a cell line responding sensitively to tetracycline by measuring the luciferase activity therein. Thus, the present inventors measured the luciferase activities of cell clones in the absence and in the presence of tetracycline.

Figure 1:
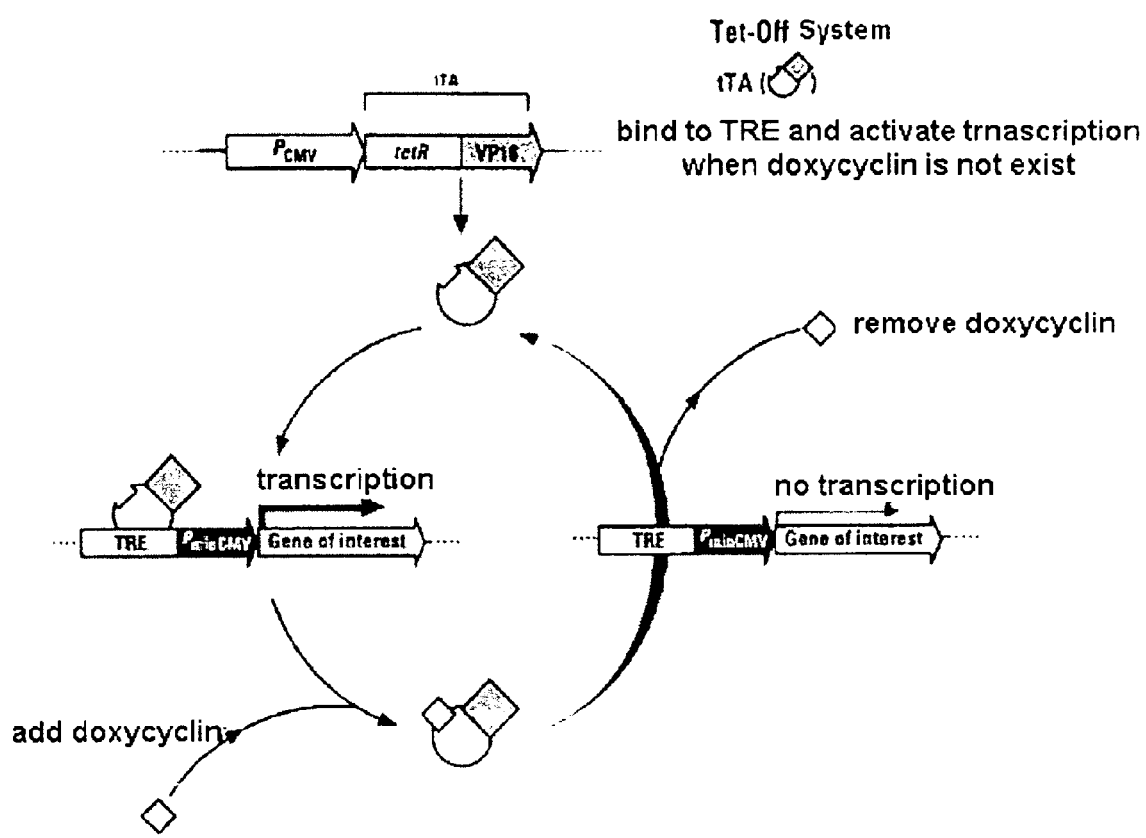
FIG. 1 is a diagram showing the Tet-Off® system.
Figure 2:
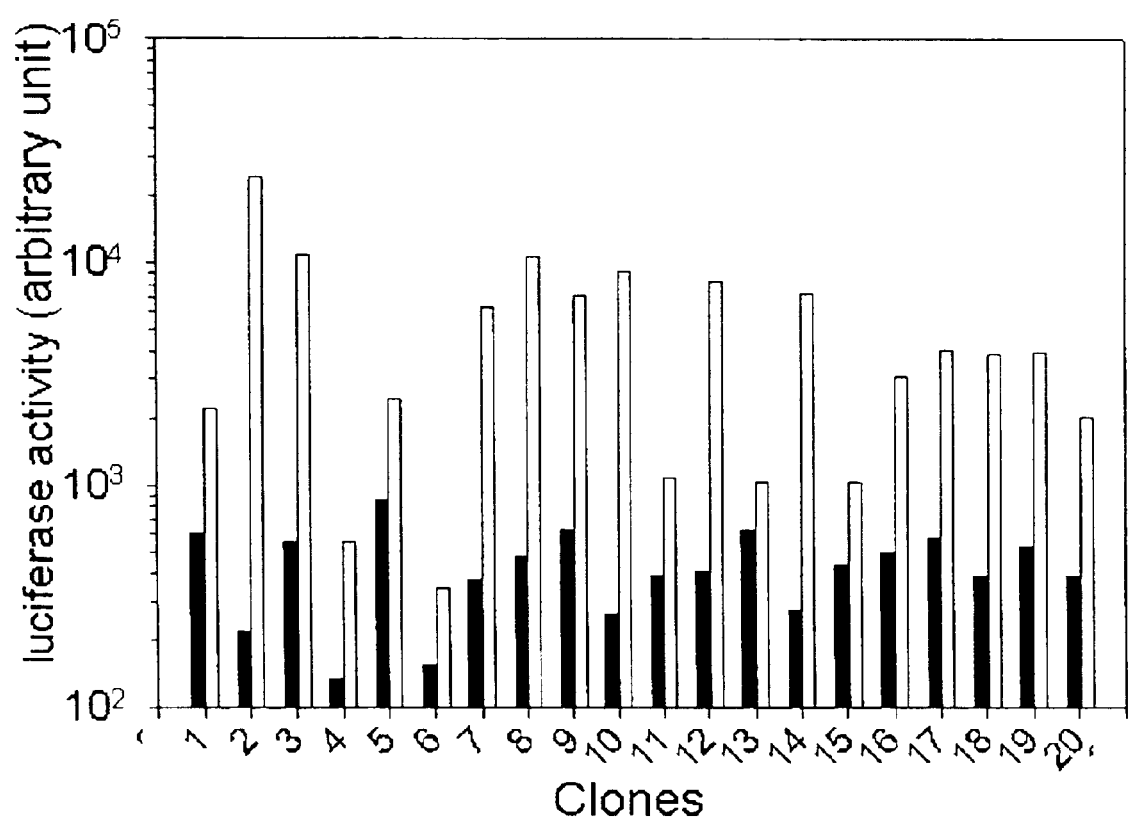
FIG. 2 is a graph showing the result of luciferase activity assay of TPO-producing cell line after Tet-Off® vector transfection.

As a result, the present inventors selected a cell line in which the luciferase activity decreased most by adding doxycycline, a kind of tetracycline, among 20 clones introduced with Tet-Off® vector and vector containing luciferase gene and named thereof "TPO-33-Tet-Off®" (FIG. 2).

Example 2

Construction of pTER-Erp57 Vector which Expresses the Erp57

The present inventors constructed Erp57 expression plasmid by inserting ERp57 cDNA into pTRE vector containing tetracycline response element to increase TPO production. ERp57 is a kind of molecular chaperones that assist in the later stages of protein biosynthesis and folding in endoplasmic reticulum (ER), and especially ERp57 is known to assist the secretion of glycoproteins. Particularly, the cDNA pool was prepared from mRNA of CHO cells and the ERp57 cDNA fragment represented by SEQ. ID. No 7 was amplified by PCR with cDNA library of CHO cell using two primers, ERp 575 represented by SEQ. ID. No 1 and ERp573 represented by SEQ. ID. No 2. The amplified ERp57 was inserted in the pT7 blue T vector (Novagen 69820-3, Germany) digested with XbaI and EcoRI, resulting in the construction of a vector that was named "pT7blueTERp57". The pT7blueT-ERp57 vector was digested with XbaI and EcoRI to elute ERp57. The ERp57 fragment inserted into PTRE vector (Clontech) was digested with XbaI and EcoRI, yielding an expression vector containing ERp57. The base sequence was analyzed with an automated DNA sequencer (ABI prism model 377, Perkin-Elmer, Foster City, Calif.) to confirm whether the amplification was done correctly.

As a result, the present inventors constructed the vector expressing tetracycline response element (referred "TRE" hereinafter) and ERp57 simultaneously, and named "pTRE-ERp57" (FIG. 3). The present inventors deposited the above expression vector, pTRE-ERp57, at the Gene Bank of Korea Research Institute of Bioscience and Biotechnology on Sep. 27, 2002 (Accession No. KCTC 10345BP).

Example 3

Construction of pBICC Vector which Simultaneously Expresses the CRT/CNX

The present inventors constructed CRT/CNX expression plasmid by inserting CRT/CNX cDNA into pBI vector to increase TPO production. CRT/CNX is another kind of molecular chaperones that assist in the later stages of protein biosynthesis and folding in endoplasmic reticulum (ER), and especially CRT/CNX is known to assist the secretion of glycoproteins. Particularly, the cDNA pool was prepared from mRNA of CHO cells and the CNX cDNA fragment represented by SEQ. ID. No 8 was amplified by PCR with cDNA library of CHO cell using two primers, cnxf represented by SEQ. ID. No 3 and cnxR represented by SEQ. ID. No 4. The amplified CNX was inserted in the pT7blue(R) vector (Novex), and then subcloned into NotI and SalI site of multicloning (MCS) II region of pBI Tet vector (Clontech), resulting in the construction of a expression vector containing CNX gene. The expression vector was named "pBIC".

Meanwhile, the CRT cDNA fragment represented by SEQ. ID. No 9 was amplified by PCR with cDNA library of CHO cell using two primers, crt5F represented by SEQ. ID. No 5 containing MluI site and Kozak sequence and crt3R represented by SEQ. ID. No 6 containing NheI site. The amplified CRT was inserted in the pT7blue(R) vector, and then subcloned into MluI and NheI site of multicloning (MCS) II region of pBI-C vector, resulting in the construction of a expression vector containing CRT/CNX gene. The expression vector was named "pBICC" (FIG. 4).

Example 4

Preparation of CHO Cell Line Containing ERp57

To prepare CHO cell line producing TPO by regulation of ERp57 by responding doxycycline, the present inventors introduced pTRE-ERp57 vector in which ERp57 expression is regulated by doxycycline, a kind of tetracycline, into TPO-33-Tet-Off® cell line, a cell line in which TPO production is regulated by doxycycline. Particularly, TPO-33-Tet-Off® cell line prepared in the above <Example 1> was co-transfected with pTRE-ERp57 vector constructed in the above <Example 2> and pTK-Hyg vector (Clontech) containing hygromicin gene using lipofectamine. The above transfected cells were cultured in IMDM media containing 500 μg/ml of hygromycin, 10% dFBS and 80 nM MTX for 2–3 weeks. During the culture, the cell clones in which ERp57 production was regulated well by the absence/presence of doxycycline, were screened by Western blot analysis and ELISA.

Figure 5:
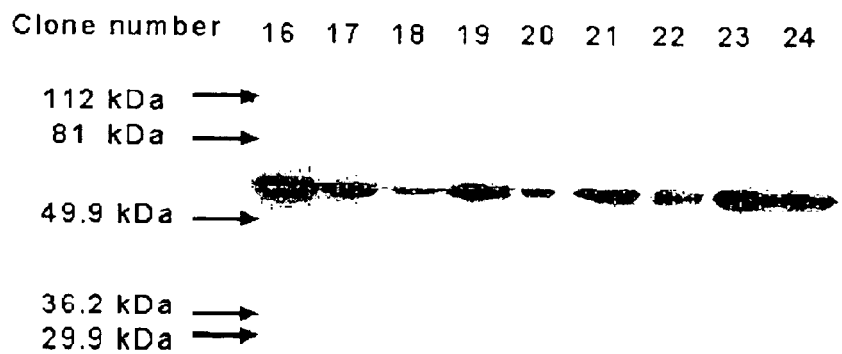
Figure 5:
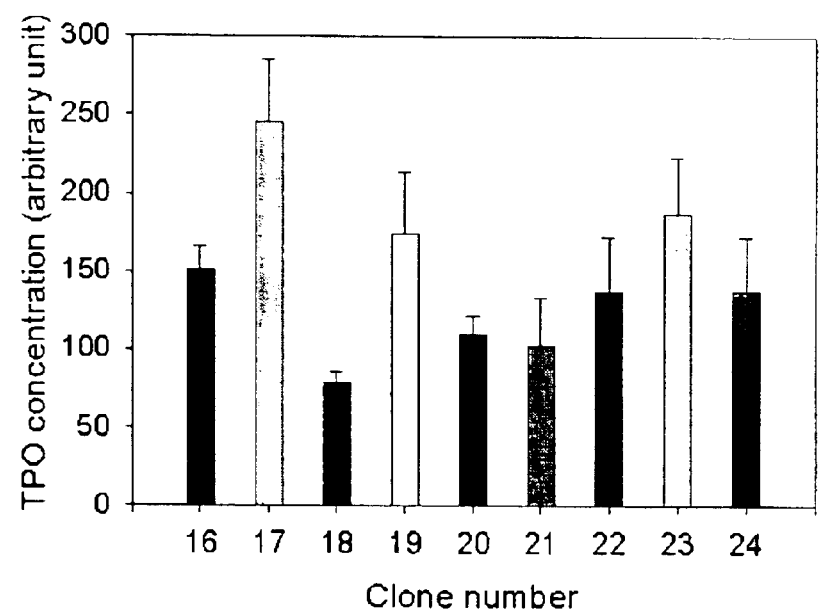
Figure 5:
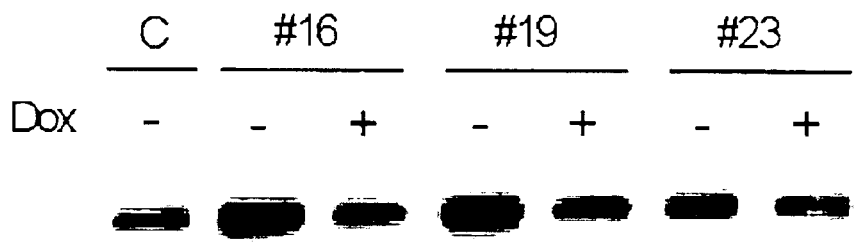

As a result, cell clones (16, 19, 23) in which ERp57 production was regulated by the absence/presence of doxycycline were selected. Among them, the clone 16 showing the most regulated ERp57 productivity was selected and named "Tet-TPO-ERp57-80*" (FIG. 5).

Example 5

Preparation of CHO Cell Line Containing CRT/CNX

To prepare CHO cell line producing TPO by regulation of CRT/CNX expression by responding doxycycline, the present inventors introduced a vector containing TRE region responding to doxycycline and CRT/CNX gene into TPO-33-Tet-Off® cell line, a cell line in which TPO production is regulated by doxycycline. Particularly, TPO-33-Tet-Off® cells were inoculated into 6 well plates at the density of $2 \times 10^5$ cells/well and cultured at 37° C. for a day. The cells were transfected with 2 μg of DNA mixture of pBICC vector regulating the expression of CRT/CNX by doxycycline and pTK-Hyg vector containing hygromycin gene (pBICC:pTK-Hyg=10:1) using lipofectamine. After 2 days of transfection, 2 μg/ml of doxycycline and 200 μg/ml of hygromycin were added into the culture medium. The medium was replaced with fresh medium every four days until colonies were grown up. 30 selected colonies were inoculated into 6 well plates (each colony/2 wells) at the density of $2 \times 10^5$ cells/well. One of the two wells was added with 2 μg/ml of doxycycline and the other was not. After 3 days of inoculation, cells were left in cell lysis buffer solution (Cell Signaling Technology, Beverly, Mass.) for 30 minutes to necrose the cells. Then the cell solution was centrifuged at 4° C. with 1,000 rpm, from which supernatants were obtained. The supernatants were inoculated onto slot blot kit and the expression of CRT was investigated using an anti-CRT antibody (Stressgen, Victoria, BC, Canada) (FIG. 6).

Figure 7:
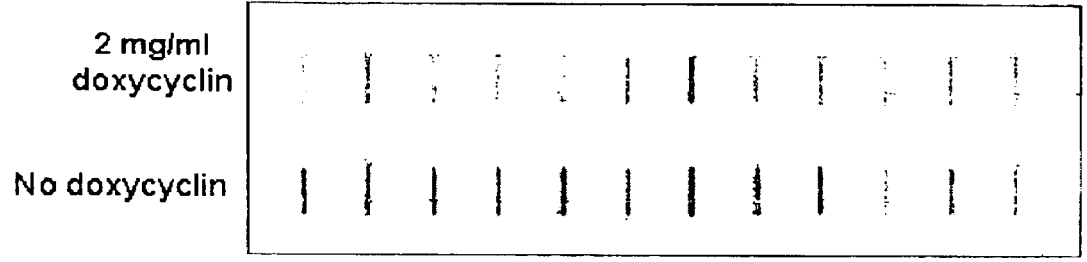
Figure 7:
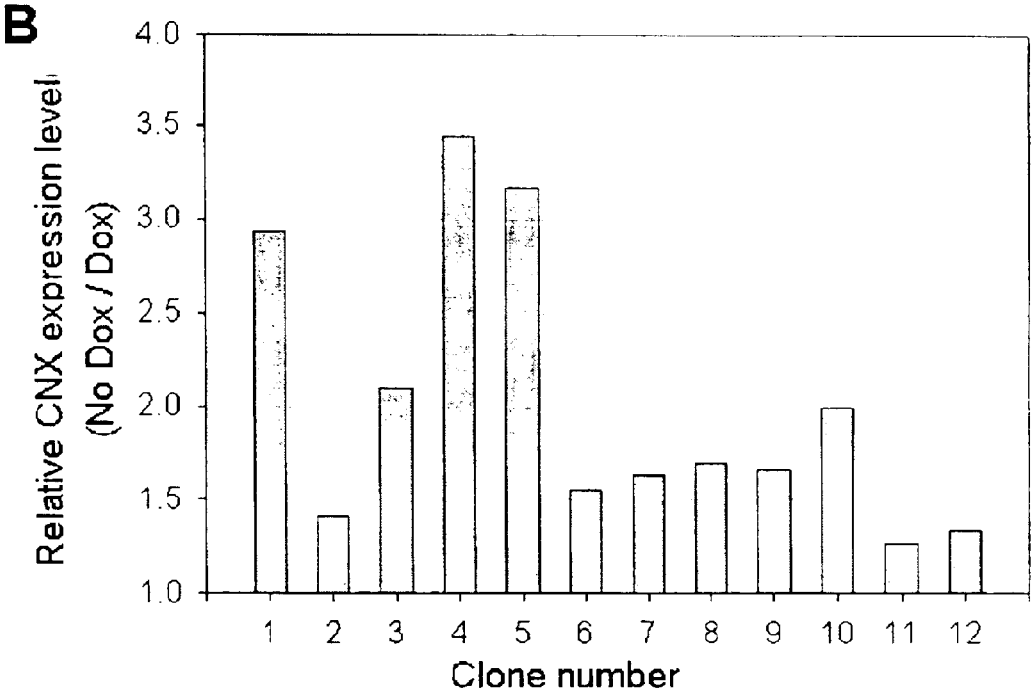

As a result, the $4^{th}$ clone showed the biggest difference in the expressed amount of CRT was selected in the presence of doxycycline and named "Tet-TPO-CC80*" (FIG. 7).

In order to confirm if the expression of CRT and CNX could be regulated by doxycycline concentration, cells were cultured with the different doxycycline concentrations from 0.001 ng/ml to 100 ng/ml. Supernatants were obtained, and the expression of CNX and CRT was investigated by Western blot analysis. As a result, it was confirmed that the expression of CRT and CNX was sensitively regulated by doxycycline concentration and there was not much difference in expression between CRT and CNX. But the expression of CRT and CNX was 2.9 and 2.8 fold higher than that of a control group in which the expression was not regulated (FIG. 8).

Example 6

The Effect of ERp57 expression on TPO Expression and CHO Cell Growth

The present inventors intended to confirm if the regulation of ERp57 expression using doxycycline could affect TPO productivity and CHO cell growth. Particularly, Tet-TPO-ERp57-80* cells obtained in the above Example 4 or TPO-33-Tet-Off® cells (control group) were inoculated into 6 well culture plates in which each well contains 3 ml of IMDM medium supplemented with 80 nM MTX and 10% dFBS at the density of $6.67 \times 10^4$ cells/well. 48 hours later, the medium was replaced with fresh IMDM medium containing 0, 0.1 and 1 μg/ml of doxycycline, 80 nM MTX and 10% dFBS. The culture medium and cells on the culture plates were obtained at regular intervals. Western blot was performed for ERp57 and ELISA was carried out for TPO.

As a result, cell growth or TPO productivity was not much affected by doxycycline concentration in a control group (FIG. 9). Meanwhile, TPO production was proportioned to the expression of ERp57 in clone #16 where Tet-TPO-ERp57 vector was introduced (FIG. 10), and the expression of ERp57 was decreased as doxycycline concentration was increased (FIG. 11). Thus, it was confirmed that the expression of ERp57 was regulated by doxycycline concentration, by which TPO production was regulated.

Based on the above results, it was confirmed that TPO productivity could be promoted by regulating the expression of ERp57 protein that stimulated production and secretion of a protein using a system that regulated gene expression with doxycycline.

Example 7

The Effect of CRT/CNX Expression on TPO Expression and CHO Cell Growth

The present inventors investigated whether the TPO productivity could be affected by the expression of CNX and CRT protein using doxycycline. Particularly, Tet-TPO-ERp57-80* cells were inoculated into 6 well culture plates in which each well contains 3 ml of IMDM medium supplemented with 80 nM MTX, 10% dFBS, 100 μg/ml of G418, and 0, 0.001, 2 μg/ml of doxycycline at the density of $2\times10^5$ cells/well and batch-cultured. The above doxycycline concentrations were determined by the values that showed high CRT expression level, medium expression level and the low expression level respectively. Cell density was measured using hemacytometer regularly. Cell culture medium was stored in a freezer for further usage. TPO productivity in the cell culture medium was measured by the ELISA kit (R&D systems).

Figure 12:
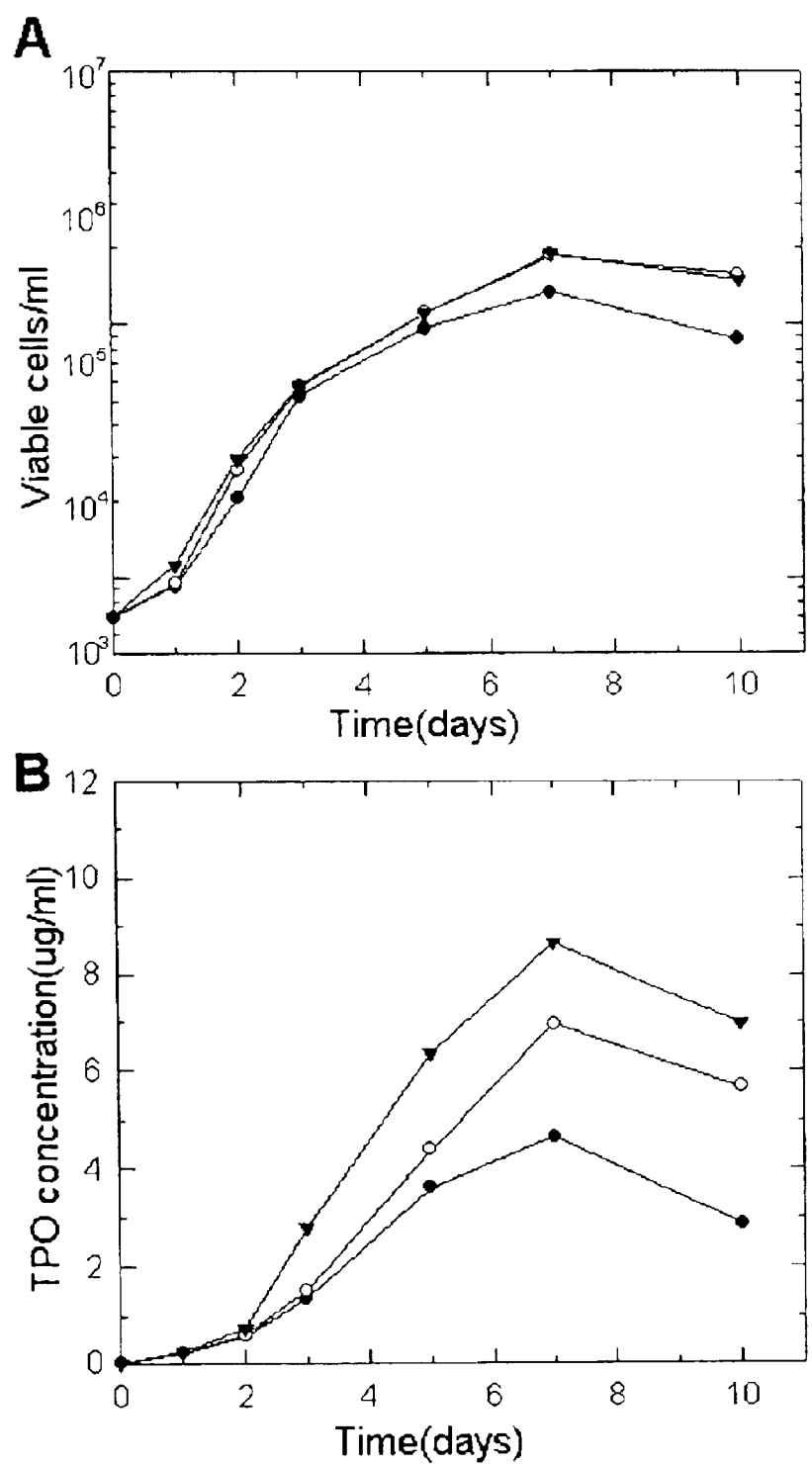

As a result, there was not much difference in cell densities among those three different concentrations of doxycycline, but TPO was produced most in the absence of doxycycline, that is, TPO productivity increased as the expression of CRT/CNX increased (FIG. 12, Table 1). Therefore, it was confirmed that the expression of CRT/CNX and TPO productivity were regulated by doxycycline concentration.

TABLE 1

| Doxycycline conc (ng/ml) | $\mu$ (/day) | Max. viable cell conc ($10^6$ cells/ml) | $q_{TPO}$ ($\mu g/10^6$ cells/day) | Max TPO titer ($\mu g/ml$) |
|---|---|---|---|---|
| 0 | 0.81 ± 0.09 | 1.90 ± 0.17 | 4.46 ± 0.41 | 8.64 ± 0.93 |
| 1 | 0.86 ± 0.04 | 1.80 ± 0.24 | 3.89 ± 0.42 | 7.84 ± 0.62 |
| 2,000 | 0.87 ± 0.07 | 1.34 ± 0.36 | 2.44 ± 0.13 | 4.66 ± 0.59 |

The above results were represented as means± standard deviations calculated from data obtained in triplicate experiments.

Example 8

The Effect of CRT/CNX Expression on the Biological Activity of TPO Produced in CHO Cells in Vivo The present inventors analyzed the effect of CRT/CNX expression on the biological activity of TPO produced in CHO cells in vivo. Particularly, Tet-TPO-CC-80* cells were inoculated into 6 well culture plates in which each well contains 3 ML of IMDM medium supplemented with 80 nM MTX, 10% dFBS, 100 μg/ml of G418, and 0, 0.001 or 2 μg/ml of doxycycline at the density of $2\times10^5$ cells/well and batch-cultured. After 3 days of cultivation, the culture medium was washed twice and then replaced with 3 ml of DMEM/F12 serum-free medium (Invitrogen) supplemented with yeastolate(Invitrogen) and 0, 0.001 or 2 μg/ml of doxycycline. Three days later, the culture solution was obtained, which was stored in a freezer for further usage. Then, TPO produced in the culture solution was measured using the ELISA kit(R&D systems). The measured TPO culture solution was injected hypodermically into female Balb/c mice with the concentration of 30 μg/kg. Five days later, blood sample was taken and the biological activity of TPO in vivo was investigated by analyzing platelet counts with a Cell-Dyn 3500 (Abbott Laboratory).

As a result, the biological activity of TPO in mice was not much different according to doxycycline concentration (FIG. 13). Therefore, it was confirmed that the biological activity of TPO was not affected by the expression of CRT/CNX.

As explained hereinbefore, when a vector regulating the expression of chaperone protein by tetracycline is introduced into animal cells, target proteins are secreted rightly, leading to the mass-production of the target proteins. Therefore, the vector can be effectively used for the production of medical substances using recombinant proteins.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An expression vector containing a gene encoding chaperone protein and tetracycline response element.

2. The expression vector as set forth in claim 1, wherein the gene encoding chaperone protein is a gene encoding ERp57 or CRT/CNX protein.

3. The expression vector as set forth in claim 2, wherein the expression vector contains a gene encoding ERp57 protein and tetracycline response element (Accession No: KCTC 10345BP).

4. The expression vector as set forth in claim 2, wherein the expression vector contains a gene encoding CRT/CNX protein and tetracycline response element.

5. A transformant prepared by transfecting a cell line producing target protein with the expression vector of claim 1.

6. The transformant as set forth in claim 5, wherein the transformant is prepared by transfecting the cell line with the expression vector of claim 3.

7. The transformant as set forth in claim 5, wherein the transformant is prepared by transfecting the cell line with the expression vector of claim 4.

8. The transformant as set forth in claim 5, wherein the cell line is characterized by that its gene expression is regulated by tetracycline.

9. The transformant as set forth in claim 5, wherein the target protein is thrombopoetin.

10. A method for mass-production of target protein comprises the following steps:

1) Constructing an expression vector of claim 1 containing a gene encoding chaperone protein and tetracycline response element;

2) Preparing a transformant by transfecting a cell line producing thrombopoetin with the expression vector of the above step 1; and 3) Culturing the transformant of the above step 2 with different concentrations of tetracycline.

11. The method as set forth in claim 10, wherein the chaperone protein is ERp57 or CRT/CNX.

12. The method as set forth in claim 10, wherein the gene encoding chaperone protein is originated from CHO cell line.

13. The method as set forth in claim 10, wherein the target protein is thrombopoetin.

14. The method as set forth in claim 10, wherein the expression of chaperone protein increases by the decrease of tetracycline concentration, resulting in the promotion of the production of the target protein.

15. The method as set forth in claim 14, wherein the tetracycline is doxycycline.

* * * * *

SEQUENCE LISTING

<160> NUMBER OF SEQ ID NOS: 9

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: ERp575 primer

<400> SEQUENCE: 1
tcacaagaat tcgccatgcg cttcagc                                        27

<210> SEQ ID NO 2
<211> LENGTH: 30
<212> TYPE: DNA
<213> ORGANISM: Artificial Sequence

```
-continued

<220> FEATURE:
<223> OTHER INFORMATION: Description of Artificial Sequence: ERp573
      primer

<400> SEQUENCE: 2
ggcggttcta gattattaga ggtcctcttg                                        30

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: cnxF primer

<400> SEQUENCE: 3
tttaatgcgg ccgccatgga agggaagtgg t                                      31

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: cnxR primer

<400> SEQUENCE: 4
taatgcgtcg actcatcatc tttcgtgg                                          28

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: crt5F
      primer

<400> SEQUENCE: 5
attactacgc gtgccatgct cctttcggtg                                        30

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: crt3R

<400> SEQUENCE: 6
atcgcggcta gctactacag ctcatcctt                                         29

<210> SEQ ID NO 7
<211> LENGTH: 1518
<212> TYPE: DNA
<213> ORGANISM: Cricetulus griseus

<400> SEQUENCE: 7
atgcgcttca gctgcctagc gctgctcccg ggcgtggcgc tgctgctcgc ctcggcccgc        60
ctcgccgccg cctctgacgt gctggaactc acggacgaaa acttcgagag tcgcgtctcc       120
gacacgggct ctgcgggcct catgctagtc gagttcttcg cccccttggtg tggacattgc      180 aagaggcttg cccctgagta tgaagctgca gcaactagat tgaaaggaat agtcccatta       240
acaaaggttg attgcactgc caacacaaac acctgtaata agtatggagt cagtggctac       300
ccaaccctta aaatatttag agatggtgaa gaagcaggtg cttatgatgg gcctaggact       360
gccgatggaa ttgtcagcca cttgaagaaa caagcagggc cagcttcggt tcttctcagg       420
```

```
tctgaggaag aatttaagaa gttcattagt gataaagatg cttcggtggt gggctttttc    480
agggatttat tcagtgacgg tcactctgaa ttcctaaaag cagccagcaa cttgagagat    540
aactacagat ttgcacacac caacgttgag tctctggtga aggagtatga tgataatgga    600 gagggatca cttatttcg tccttcacat cttgctaaca agtttgaaga caaaactgtg    660
gtatatactg aacagaaaat gaccagtggc aagataaaaa ggtttatcca ggaaagcatt    720
tttggtatct gtcctcatat gacagaagac aataaagatt tgatacagag caaggactta    780
cttacagcct actatgatgt tgactatgaa agaatgcta aaggttccaa ctattggaga    840
aacagagtga tgatggtggc aaaaaaattc ctggatgctg acacaaaact caactttgct    900
gtagctagcc gtaaaacctt tagccatgag ctgtccgact ttggcttaga aagcactact    960
ggagaggttc ctgttgtagc aatcagaact gctaaaggag agaagtttgt catgcaggaa   1020
gagttctcga gggacgggaa ggctctggag cggttcctgc aggattactt tgatggcaac   1080
ctgaagagat acctcaagtc tgaacctatc ccagagacca acgatgggcc tgtcaaggtt   1140
gtggtagcag aaaattttga tgacatagtg aataatgaag ataaggatgt gctgattgaa   1200
ttttatgccc cttggtgtgg tcactgtaag aatctggagc ccaaatataa agaactggga   1260
gagaaactca gcaaagaccc aaatattgtt atagccaaga tggatgccac agctaatgat   1320
gtgccttctc catatgaagt caaaggtttt cctaccatct acttttcacc agccaacaag   1380
aagctaaatc caaagaagta tgaaggtggc cgtgaattaa atgattttat taactatcta   1440
caacgagaag ctacaaccc ccctataatt caagaagaaa aacccaagaa gaagaagaag   1500
gcacaagagg acctctaa                                                 1518

<210> SEQ ID NO 8
<211> LENGTH: 1776
<212> TYPE: DNA
<213> ORGANISM: Cricetulus griseus
<220> FEATURE:
<221> NAME/KEY: misc_feature
<222> LOCATION: (854)
<223> OTHER INFORMATION: n represents any of the nucleotide, A, T, G and
      C

<400> SEQUENCE: 8
atggaaggga agtggttact gtgtttactc ctggtccttg gaactgtagc tgttcaggct     60
catgatggac atgatgatga catgattgat attgaagatg atcttgatga tgttattgaa    120
gaggtagaag attcgaaatc gaaatcagat tccagtactc ctccatctcc aaaggttacc    180
tacaaagctc cagttccaac aggggaggtt tattttgctg actcctttga cagagggtct    240
ctatcagggt ggattttatc taaagccaaa aaagatgaca ctgatgatga aattgccaaa    300
tatgatggaa agtgggaggt agatgaaatg aaggacacaa agcttccagg tgataaagga    360
cttgtactga tgtctcgggc caagcatcat gccatctctg ctaaactgaa caagcccttc    420
ctgtttgata ccaagcctct cattgttcag tatgaggtta attttcagaa tggcatagaa    480
tgtggtggtg cctatgtgaa gctgctttcc aagcctcag aactcaactt ggatcaattc    540
cacgacaaga ctccctatac tattatgttt ggtccagata aatgtggaga agactacaaa    600
ctgcacttca tctttcgcca caaaaacccc aagacaggtg tatatgaaga aaagcatgct    660
aagaggccag atacagatct gaagatctat tttactgaca agaaaactca tctttacaca    720
ttaatcttga atccagacaa tagttttgaa atattagttg accagtatgt tgtgaacagt    780
ggaaatctgc taaatgacat gactcctgct gtaaacccctt cacgtgaaat tgaggaccca    840
```

```
                                               -continued
gaagaccaga agcntgagga ttgggatgaa agacccaaaa tcccagatcc ggatgctgtc     900
aagccagatg attgggatga agatgcccct ggtaagattc cagatgaaga ggccacaaag     960
cctgaaggct ggttagatga tgagcctgag tatattccag accctgatgc ggacaagcca    1020
gaggattggg atgaggatat ggatggagaa tgggaggctc ctcagattgc caaccctaaa    1080
tgtgagtcag cccctggggt ggagtctgg cagcgacctt tgattgacaa tcccaattat    1140
aagggcaaat ggaagcctcc catgattgac aatcctaact accagggagt ctggaaacca    1200
aggaaaatac caaatccaga tttctttgaa gatctagaac cttttaagat gacgcctttc    1260
agtgctattg gtttggagct ctggtccatg acttctgaca tctttttttga caactttatc    1320 attagtggtg accgaagagt agttgacgat tgggccaatg atgggtgggg cctgaagaaa    1380
gctgctgatg ggctgctga gccaggtgta gtggggcata tgctggaggc agctgaagag    1440
cgtccgtggc tctgggtggt ctacattctg actgtagctt tgccagtgtt ccttgtgatc    1500
ctattctgct gctctggaaa gaaacagtcc aatgctatgg agtacaagaa gacggatgct    1560
gcccagccag atgtgaagga agatgaaggg aaggaagaag agaagaacaa ggggggatgaa    1620 gaggaagaag aagagaagct tgaagagaaa cagaaaagtg atgctgaaga gatggtggc    1680 actggcagtc aagatgagga agatagaaaa cccacagcag aggaggatga aattttgaac    1740
agatcaccaa gaaacagaaa gccacgaaga gagtga                              1776

<210> SEQ ID NO 9
<211> LENGTH: 1254
<212> TYPE: DNA
<213> ORGANISM: Cricetulus griseus

<400> SEQUENCE: 9
atgctccttt ccgtgccgct cctgctcggc ctcctcggcc tggccgccgc ggaacctgcc      60
gtctatttca aagagcagtt cttggacgga gatgactgga ccaaccgctg ggtcgaatcc     120
aaacacaagt ccgattttgg caaatttgtc ctcagttctg gcaaattcta cggggaccag     180
gagaaggata aagggctgca gacaagccag gatgcccgat tttacgcgct gtccgctaga     240
ttcgaaccct tcagcaacaa gggccagaca ctggtggtac agttcacggt gaagcatgag     300
cagaacatcg actgtggggg tgggtatgtg aagctgtttc cgggtagttt ggaccagaag     360
gacatgcatg gagactcgga atacaacatc atgtttggtc cggacatctg tggtcctggc     420
accaagaagg ttcatgtcat ctttaactac aagggcaaga atgtgctgat caacaaggat     480
atccggtgta aggatgatga attcacacac ctgtacacgc tgattgtgcg gccagacaac     540
acctatgagg tgaaaattga caacagccag gtggagtcag gctccttgga ggatgattgg     600
gactttctgc cacccaagaa gataaaggac cctgatgctg ccaagccgga agactgggat     660
gaacgagcca gatcgatga ccccacagat tccaagcctg aggactggga caagccagag     720
cacatccctg accctgatgc taagaagcct gaggactggg atgaagagat ggatggagag     780
tgggaaccac cagtgattca aaatcctgaa tacaagggcg agtggaaacc acgtcaaatt     840
gacaacccga attacaaggg tacctggata cacccagaaa ttgacaaccc tgaatactcc     900
cccgatgcaa atatctatgc ctatgacagt tttgctgtac tgggcttaga tctctggcag    960
gtcaagtctg gcacaatctt tgacaacttt ctcatcacca atgatgaagc ctatgcagag    1020
gagtttggca atgagacatg gggtgtcacc aaggcttcag aaaagcagat gaaggacaag    1080
caggatgagg agcagaggct gaaggaagaa gaagaagaca agaagcgtaa agaggaggaa    1140
```

```
gaggctgagg acaaagagga tgaggatgac agagatgaag atgaagaaga tgaggatgag    1200
aaggaggaag atgaggagga tactacccct ggccagacca aggatgagct gtag          1254
```